United States Patent
Yoshinaga et al.

(10) Patent No.: US 12,137,885 B2
(45) Date of Patent: Nov. 12, 2024

(54) BODILY FLUID COLLECTION DEVICE

(71) Applicant: SENJU PHARMACEUTICAL CO., LTD., Osaka (JP)

(72) Inventors: Ryo Yoshinaga, Osaka (JP); Tatsuya Sakai, Osaka (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 17/791,787

(22) PCT Filed: Mar. 26, 2021

(86) PCT No.: PCT/JP2021/012790
§ 371 (c)(1),
(2) Date: Jul. 8, 2022

(87) PCT Pub. No.: WO2021/193902
PCT Pub. Date: Sep. 30, 2021

(65) Prior Publication Data
US 2023/0140127 A1 May 4, 2023

(30) Foreign Application Priority Data

Mar. 27, 2020 (JP) .................................. 2020-057938

(51) Int. Cl.
*A61B 10/00* (2006.01)
*A61B 5/15* (2006.01)

(52) U.S. Cl.
CPC .... *A61B 10/0045* (2013.01); *A61B 5/150106* (2013.01); *A61B 5/150396* (2013.01); *A61B 5/150946* (2013.01)

(58) Field of Classification Search
CPC .......... A61B 10/0045; A61B 5/150106; A61B 5/150396; A61B 5/150946;
(Continued)

(56) References Cited

U.S. PATENT DOCUMENTS 4,133,304 A * 1/1979 Bailey ............... A61B 5/150511
600/577
4,228,808 A * 10/1980 Marsoner ......... A61B 5/150503
600/576
(Continued)

FOREIGN PATENT DOCUMENTS

JP 9-94231 4/1997
JP 2005-237617 9/2005
(Continued)

OTHER PUBLICATIONS

International Search Report issued May 11, 2021 in International (PCT) Application No. PCT/JP2021/012790.
(Continued)

*Primary Examiner* — Benjamin S Melhus
*Assistant Examiner* — Severo Antonio P Lopez
(74) *Attorney, Agent, or Firm* — Wenderoth, Lind & Ponack, L.L.P (57) ABSTRACT

A bodily fluid collection device includes a needle part having a needle tube with a needle tip, and a capillary removably connected to a base end part of the needle tube in a longitudinal direction thereof on a side opposite to the needle tip. A method for collecting a bodily fluid using the bodily fluid collection device, and a method for collecting an aqueous humor using the bodily fluid collection device are also disclosed.

8 Claims, 6 Drawing Sheets

(58) Field of Classification Search
CPC ........ A61B 5/150389; A61B 5/150381; A61B 5/150374; A61B 5/150412; A61B 5/150419; A61B 5/150343; A61B 5/150007

See application file for complete search history.

(56) References Cited

U.S. PATENT DOCUMENTS

| | | | | |
|---|---|---|---|---|
| 5,080,865 | A | * | 1/1992 | Leiner ..................... G01N 1/28 204/411 |
| 7,772,006 | B2 | | 8/2010 | Tornambe et al. |
| 2004/0069076 | A1 | * | 4/2004 | Gamble ................. G01N 35/10 73/864.91 |
| 2015/0209180 | A1 | * | 7/2015 | Prausnitz ......... A61B 5/150396 604/521 |
| 2016/0287219 | A1 | | 10/2016 | Zhao |
| 2018/0074074 | A1 | * | 3/2018 | Luloh ................ G01N 33/6869 |
| 2018/0078415 | A1 | | 3/2018 | Citterio et al. |

FOREIGN PATENT DOCUMENTS

| | | |
|---|---|---|
| JP | 2009-136485 | 6/2009 |
| JP | 3210169 | 5/2017 |
| JP | 2020-024194 | 2/2020 |

OTHER PUBLICATIONS

Miller et al., "Fleroxacin Pharmacokinetics in Aqueous and Vitreous Humors Determined by Using Complete Concentration-Time Data from Individual Rabbits", Antimicrobial Agents and Chemotherapy, Jan. 1992, vol. 36, No. 1, pp. 32-38.

International Preliminary Report on Patentability issued Jun. 1, 2022 in International (PCT) Application No. PCT/JP2021/012790.

* cited by examiner

Method 1: average value・standard deviation (n=3-4)
Method 2: average value (n=4)

BODILY FLUID COLLECTION DEVICE

TECHNICAL FIELD

The present invention relates to a bodily fluid-collecting device and a method for collecting a bodily fluid using the same.

BACKGROUND ART

JP 2005-237617 A discloses a conventional bodily fluid-collecting device. The bodily fluid-collecting device disclosed in JP 2005-237617 A is composed of an injection syringe. In the bodily fluid-collecting device of JP 2005-237617 A, an injection needle is inserted into a living body, and a piston is pulled to thereby draw a bodily fluid into a cylinder body.

SUMMARY OF INVENTION

Technical Problem

An object of the present invention is to provide a bodily fluid-collecting device that is capable of collecting a fixed amount of bodily fluid while minimizing damage to a living body, a method for collecting a bodily fluid using the device, and a method for collecting an aqueous humor using the device.

Solution to Problem

As one embodiment according to the present invention, the following bodily fluid-collecting device is provided.

Item 1-1. A bodily fluid-collecting device comprising:
a needle part having a needle tube with a needle tip; and
a capillary removably connected to a base end part of the needle tube in its longitudinal direction on a side opposite to the needle tip.

Item 1-2. The bodily fluid-collecting device according to Item 1-1, wherein the needle part has a holding part that is in contact with the outer peripheral surface of the needle tube to hold the needle tube,
the base end part of the needle tube protrudes from the holding part in the longitudinal direction of the needle tube, and
the capillary is connected to the base end part while being fitted with the base end part.

Item 1-3. The bodily fluid-collecting device according to Item 1-2, wherein the protrusion dimension of the base end part from the holding part is 1 mm or more and 13 mm or less.

Item 1-4. The bodily fluid-collecting device according to Item 1-2 or 1-3, wherein the inner diameter of the capillary is the same as the outer diameter of the base end part.

Item 1-5. The bodily fluid-collecting device according to any one of Items 1-1 to 1-4, wherein the needle tube has an outer diameter of 0.18 mm or more and 0.30 mm or less.

Item 1-6. The bodily fluid-collecting device according to Item 1-1, wherein the needle part has a needle hub that supports the needle tube;
the needle hub has:
a holding part that is in contact with the outer peripheral surface of the needle tube to hold the needle tube, and
a cylindrical part that leads to the holding part and into which the capillary is removably fitted; and
the capillary is connected to the base end part while being fitted into the cylindrical part.

Item 1-7. The bodily fluid-collecting device according to Item 1-1, wherein the needle part has a needle hub that supports the needle tube;
the needle hub has:
a holding part that is in contact with the outer peripheral surface of the needle tube to hold the needle tube,
a cylindrical part leading to the holding part, and
a holding member disposed inside the cylindrical part and removably holding the capillary; and
the capillary is connected to the base end part while being held by the holding member.

Item 1-8. The bodily fluid-collecting device according to any one of Items 1-1 to 1-7, wherein the needle part has a needle hub that supports the needle tube; and
the bodily fluid-collecting device further comprises a protective member attached to the needle hub and covering the circumference of the capillary.

Item 1-9. A bodily fluid-collecting device comprising:
a needle part having a needle tube with a needle tip; and
a capillary removably connected to a base end part of the needle tube in its longitudinal direction on a side opposite to the needle tip,
wherein the needle part has a holding part that is in contact with the outer peripheral surface of the needle tube to hold the needle tube,
the base end part of the needle tube protrudes from the holding part in the longitudinal direction of the needle tube,
the capillary is connected to the base end part while being fitted with the base end part,
the protrusion dimension of the base end part from the holding part is 1 mm or more and 13 mm or less,
the inner diameter of the capillary is the same as the outer diameter of the base end part,
the needle tube has an outer diameter of 0.18 mm or more and 0.30 mm or less,
the needle part has a needle hub that supports the needle tube, and
the bodily fluid-collecting device further comprises a protective member attached to the needle hub and covering the circumference of the capillary.

As another embodiment of the present invention, the following method for collecting a bodily fluid is provided.

Item 2-1. A method for collecting a bodily fluid using the bodily fluid-collecting device according to any one of Items 1-1 to 1-9, the method comprising the steps of:
inserting the needle tip of the needle tube into a tissue of a living body where the bodily fluid is present;
withdrawing the needle tip from the tissue after the capillary is filled with the bodily fluid;
removing the capillary from the needle tube; and
extracting the bodily fluid filled in the capillary.

Item 2-2. A method for collecting a bodily fluid using the bodily fluid-collecting device according to Item 1-9, the method comprising the steps of:
inserting the needle tip of the needle tube into a tissue of a living body where the bodily fluid is present;
withdrawing the needle tip from the tissue after the capillary is filled with the bodily fluid;
removing the needle part from the protective member;
removing the capillary from the needle tube; and
extracting the bodily fluid filled in the capillary.

As still another embodiment of the present invention, the following method for collecting an aqueous humor is provided.

Item 3-1. A method for collecting an aqueous humor using the bodily fluid-collecting device according to any one of Items 1-1 to 1-9, the method comprising the steps of:
- inserting the needle tip of the needle tube into an anterior chamber of a living body;
- withdrawing the needle tip from the anterior chamber after the capillary is filled with the aqueous humor;
- removing the capillary from the needle tube; and
- extracting the aqueous humor filled in the capillary.

Item 3-2. A method for collecting an aqueous humor using the bodily fluid-collecting device according to Item 1-9, the method comprising the steps of:
- inserting the needle tip of the needle tube into an anterior chamber of a living body;
- withdrawing the needle tip from the anterior chamber after the capillary is filled with the aqueous humor;
- removing the needle part from the protective member;
- removing the capillary from the needle tube; and
- extracting the aqueous humor filled in the capillary.

Advantageous Effects of Invention

The bodily fluid-collecting device, method for collecting a bodily fluid using the device, and method for collecting an aqueous humor using the device of the above embodiments according to the present invention are advantageous in that a fixed amount of bodily fluid can be collected while minimizing damage to a living body.

BRIEF DESCRIPTION OF DRAWINGS

FIGS. 4 (A) and (B) are explanatory drawings for explaining the third step of a method for collecting an aqueous humor using the bodily fluid-collecting device.

FIG. 5 (A) is a cross-sectional view of a bodily fluid-collecting device according to Modified Example 1 in a plane along the longitudinal direction of a needle tube. FIG. 5 (B) is a cross-sectional view of a bodily fluid-collecting device according to Modified Example 2 in a plane along the longitudinal direction of a needle tube. FIG. 5 (C) is a cross-sectional view of a bodily fluid-collecting device according to Modified Example 3 in a plane along the longitudinal direction of a needle tube.

DESCRIPTION OF EMBODIMENTS (1) Embodiment (1.1) Outline

The bodily fluid-collecting device 1 according to the present embodiment is a device that collects a fixed amount of bodily fluid from a living body. The "living body" as used herein includes animals including mammals. Examples of mammals include humans, monkeys, pigs, dogs, cats, rabbits, guinea pigs, rats, mice, and the like. The bodily fluid-collecting device 1 according to the present embodiment may be used for any test, examination, diagnosis, etc., and may be used, for example, in a non-clinical (preclinical) test or a clinical test. The "bodily fluid" is preferably one that can be examined by the collection of a small and fixed amount thereof, but is not particularly limited thereto. Examples of the bodily fluid include an aqueous humor 73 (hydatoid), blood, spinal fluid (cerebrospinal fluid), lymph fluid, body cavity fluids (pleural fluid, ascitic fluid, etc.), digestive fluids (gastric juice, bile, pancreatic juice, intestinal juice, etc.), and the like. In the present embodiment, the aqueous humor 73 of an animal is explained as an example of the bodily fluid.

The bodily fluid-collecting device 1 according to the present embodiment can collect a small and fixed amount of aqueous humor 73 from an animal as a living body. The collected aqueous humor 73 can be examined, for example, to evaluate the concentrations of drugs, biogenic components, and the like contained in the aqueous humor 73. Since the bodily fluid-collecting device 1 according to the present embodiment can collect only a small amount of aqueous humor 73 required for examination, the aqueous humor 73 can be repeatedly and sequentially collected from one living body. Therefore, the use of the bodily fluid-collecting device 1 according to the present embodiment is advantageous in that it is possible to obtain sequential data for each individual living body and to avoid errors in data interpretation due to individual variations. Further, only the necessary amount of bodily fluid used for analysis can be quantitatively collected from a living body and used directly for analysis, thus minimizing the amount of bodily fluid collected. As a result, collection can be completed quickly even when using a needle tube 3 that is thinner than conventional ones. Further, the use of the thinner needle tube 3 can minimize damage to the living body. In addition, the small amount of bodily fluid collected at one time also contributes to the minimization of damage to the living body. Moreover, when using the bodily fluid-collecting device 1 according to the present embodiment, which takes advantage of the effect of capillary action for collection, it is not necessary to pull the plunger like before, which can improve workability. In addition, it is possible to eliminate damage to the living body caused by the negative pressure generated by pulling the plunger. This also contributes to the minimization of damage to the living body. When using the bodily fluid-collecting device 1 according to the present embodiment, even in the case of one bodily fluid collection as before, injury to the living body can be reduced, and damage to the living body can be minimized. Further, due to the advantage of less damage to the living body, the bodily fluid can be repeatedly and sequentially collected from one living body.

Figure 1:
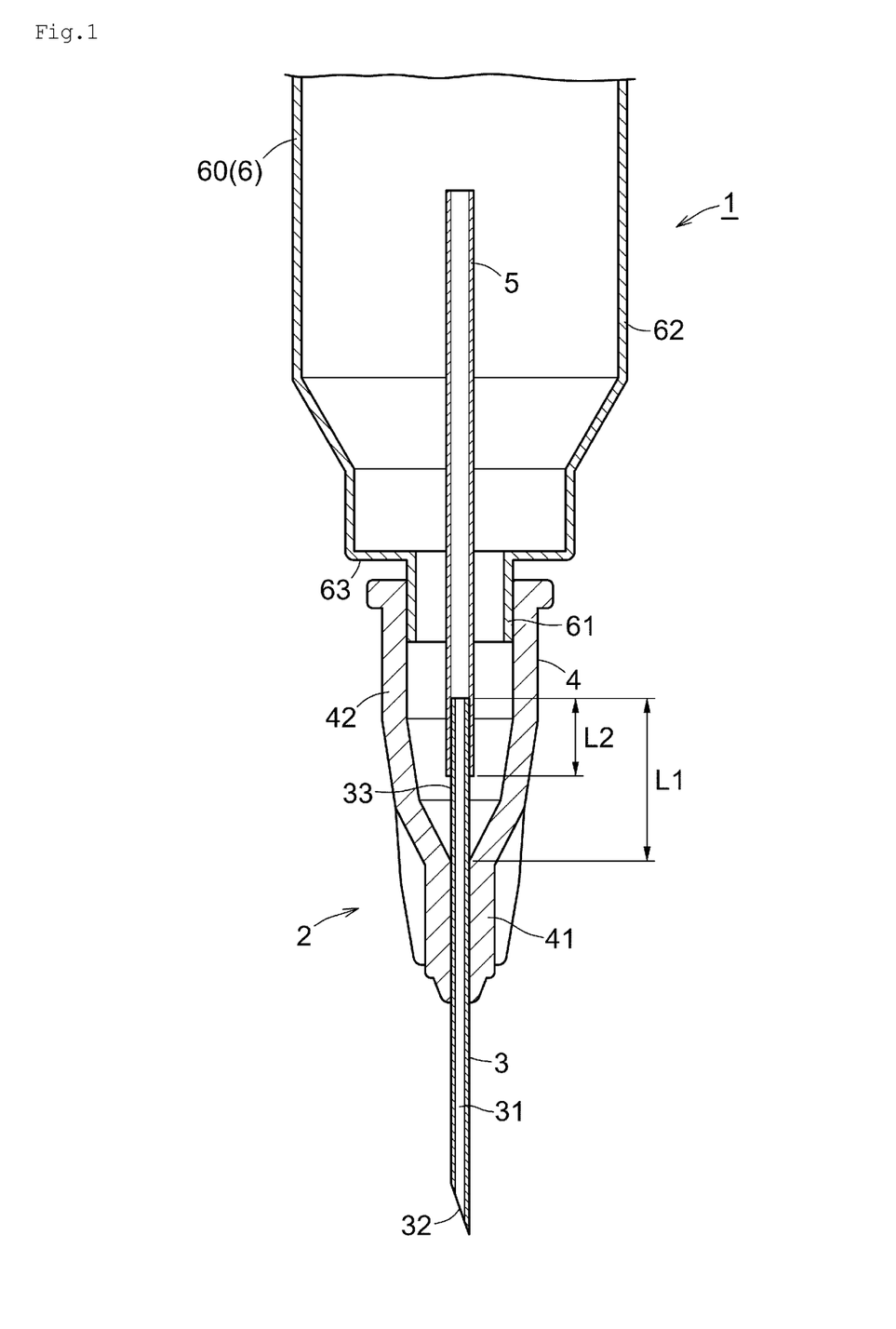
FIG. 1 is a cross-sectional view of a bodily fluid-collecting device according to one embodiment of the present invention in a plane along the longitudinal direction of a needle tube.

The bodily fluid-collecting device 1 comprises a needle part 2 having a needle tube 3, and a capillary 5, as shown in FIG. 1. The needle tube 3 has a needle tip 32 to be inserted into the target site of a living body. The capillary 5 is removably connected to, of the end parts of the needle tube 3 in its longitudinal direction, an end part on a side opposite to the needle tip 32 (hereinafter referred to as "base end part 33").

For example, when the user inserts the needle tip 32 of the needle tube 3 into an anterior chamber 72 as the target site of a living body, an aqueous humor 73 is drawn into the needle tube 3 by the effect of capillary action. Then, the aqueous humor 73 reaches the capillary 5. The aqueous humor 73 reaching the capillary 5 moves in the capillary 5 toward an end part thereof in its longitudinal direction on a side opposite to the needle tube 3 by the effect of capillary action, and fills the inside of the capillary 5. Then, the user removes the capillary 5 from the needle tube 3, and extracts the aqueous humor 73 filled in the capillary 5.

Thus, the amount of bodily fluid filled in the capillary 5 is always constant depending on the volume of the capillary 5. Therefore, according to the bodily fluid-collecting device 1, a fixed amount of bodily fluid collected from a living body can be directly used for examination. The term "directly" as used herein means that the entire amount of bodily fluid filled in the capillary 5 is used as is for examination. For example, it does not include collecting a larger amount of bodily fluid from a living body and then using a fixed amount of the collected bodily fluid for examination. When using the bodily fluid-collecting device 1 according to the present embodiment, it is possible not only to repeatedly and sequentially collect a bodily fluid from one living body, but also to accurately collect a fixed amount of bodily fluid at all times, which can improve the accuracy of examination.

(1.2) Configuration

Figure 2:
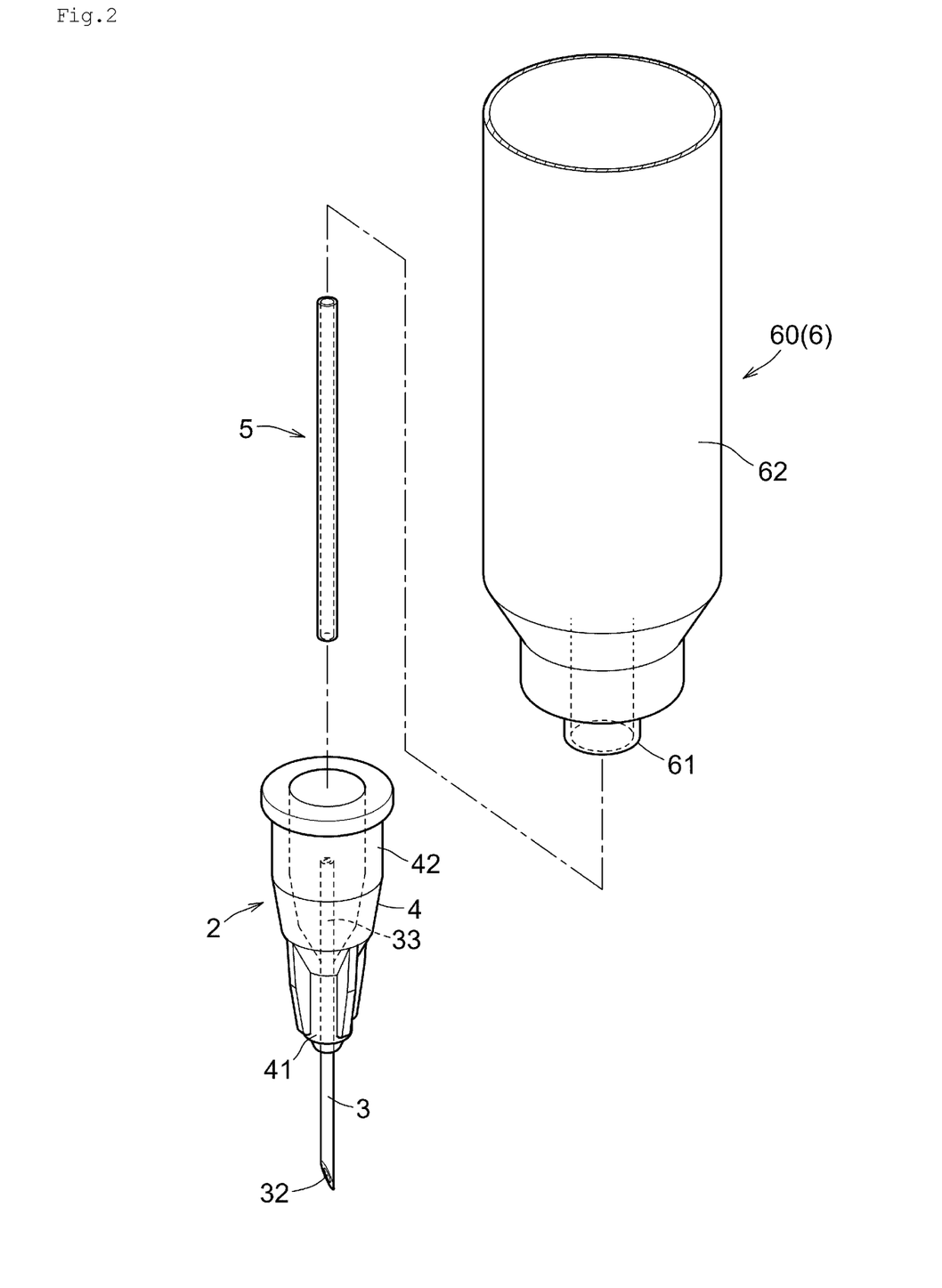
FIG. 2 is an exploded perspective view of the bodily fluid-collecting device.

The bodily fluid-collecting device 1 according to the present embodiment is described in detail below. The bodily fluid-collecting device 1 comprises a needle part 2, a capillary 5, and a protective member 6, as shown in FIG. 2. Here, a protector for protecting the needle tip 32 is not attached to the bodily fluid-collecting device 1; however, the bodily fluid-collecting device 1 according to the present invention may comprise such a protector.

(1.2.1) Needle Part

The needle part 2 is a single component having a needle tube 3. The needle part 2 is composed of, for example, an injection needle, and is removably attached to the protective member 6. The needle part 2 comprises the needle tube 3 and a needle hub 4.

One tip part of the needle tube 3 is to be inserted into a living body. The needle tube 3 is composed of a linearly formed thin tube. The tip (needle tip 32) of the needle tube 3 is cut along a plane inclined with respect to the axial direction (longitudinal direction) of the needle tube 3. The shape of the needle tip 32 is not particularly limited, and examples include a single point, a Huber point, a lancet point, a back cut point, and the like. In the inside of the needle tube 3, a flow path 31 through which the bodily fluid passes is formed, as shown in FIG. 1. The flow path 31 is continuous from one end to the other along the longitudinal direction of the needle tube 3.

Examples of the material of the needle tube 3 include, but are not particularly limited to, stainless, stainless steel (e.g., SUS304 and SUS316L), aluminum alloys, titanium, titanium alloys, synthetic resin, and the like. The outer diameter of the needle tube 3 is preferably, for example, 0.18 mm or more and 0.30 mm or less, and more preferably 0.18 mm, in terms of collecting the aqueous humor 73 of the living body. The outer diameter of the needle tube 3 is preferably smaller because damage to the cornea 71 of the living body can be suppressed; however, if the outer diameter of the needle tube 3 is less than 0.18 mm, it may not be possible to easily puncture the cornea 71 of the living body, in terms of the strength of the needle tube 3. In contrast, if the outer diameter of the needle tube 3 exceeds 0.30 mm, damage to the cornea 71 of the living body is large, and the burden on the living body increases. However, in the present invention, the appropriate size of the outer diameter of the needle tube 3 depends on the type, size, or bodily fluid collection site of the living body, and is thus not particularly limited.

The needle hub 4 is a portion supporting the needle tube 3. The needle hub 4 may function as a portion directly held by the user while supporting the needle tube 3; however, it is preferable that the needle hub 4 is attached to the protective member 6 to fix the needle tube 3 to the protective member 6. The shape of the needle hub 4 can be selected depending on the shape of a tip part 61 of the protective member 6, and may be, for example, a standard type (e.g. screw type) or a luer-lock type. The material of the needle hub 4 is not particularly limited, and examples include synthetic resin, metal, and the like. The needle hub 4 comprises a holding part 41 and a cylindrical part 42, as shown in FIG. 1.

The holding part 41 is in contact with the outer peripheral surface of the needle tube 3 to hold the needle tube 3. The needle tube 3 is held by the holding part 41, for example, by mating, screwing, bonding, fusing, welding, insert molding, dichromatic molding, or the like.

The holding part 41 holds a middle portion of the needle tube 3 in its longitudinal direction. That is, the end part of the needle tube 3 on the side opposite to the needle tip 32 is not held by the holding part 41, and protrudes from the holding part 41. In the present embodiment, the portion protruding from the holding part 41 is defined as "base end part 33." The dimension of the base end part 33 of the needle tube 3 (hereinafter also referred to as "protrusion dimension L1") is preferably 1 mm or more and 13 mm or less, and more preferably 4 mm or more and 6 mm or less. If the protrusion dimension of the base end part 33 is less than 1 mm, a capillary 5, described later, cannot be properly supported, which is not preferable. In contrast, if the protrusion dimension L1 of the base end part 33 exceeds 13 mm, the edge of the base end part 33 may protrude from the cylindrical part 42, and the base end part 33 of the needle tube 3 may be damaged during transport or use. That is, the base end part 33 of the needle tube 3 preferably fits within the cylindrical part 42.

The cylindrical part 42 is a portion extending in a cylindrical shape from the holding part 41, and its inner diameter is famed to be larger than the inner diameter of the holding part 41. The cylindrical part 42 preferably covers the circumference of the connection part between the needle tube 3 and the capillary 5. The user can hold the cylindrical part 42 to thereby collect the bodily fluid without attaching the protective member 6; however, in the present embodiment, the user can hold the protective member 6 attached to the cylindrical part 42 to thereby collect the bodily fluid.

The cylindrical part 42 is integrally formed from an end part of the holding part 41 on the side of the base end part 33 in the longitudinal direction of the needle tube 3. The cylindrical part 42 is formed in a cylindrical shape, and there is a gap between the cylindrical part 42 and the base end part 33 of the needle tube 3 (i.e., the cylindrical part 42 is separated from the base end part 33). The tip part 61 of the protective member 6 is fitted into the opening end of the cylindrical part 42, whereby the cylindrical part 42 is attached to the tip part 61 of the protective member 6. The opening end part of the cylindrical part 42 is formed as a flange, and faces an end surface (tip surface 63) of the protective member 6 in its longitudinal direction when the needle part 2 is attached to the protective member 6. The opening end part of the cylindrical part 42 and the tip surface 63 of the protective member 6 may have a gap between them, or may be in contact with each other.

(1.2.2) Capillary

The capillary 5 is removably connected to the base end part 33 of the needle tube 3. When a liquid (bodily fluid) enters the capillary 5 at one end part in its longitudinal direction, the liquid penetrates by the effect of capillary action, and the liquid level of the liquid moves towards the other end part in the longitudinal direction.

The dimension of the capillary 5 in its longitudinal direction (length dimension) is not particularly limited, and is set depending on the volume of liquid that can be contained inside the capillary 5 (hereinafter referred to as "fluid collection volume"). The fluid collection volume of the capillary 5 is 0.25 μl or more and 200 μl or less, preferably 5 μl or more and 50 μl or less, and more preferably 5 μl or more and 20 μl or less. The length dimension of the capillary 5 is 30 mm or more and 130 mm or less, preferably 30 mm or more and 100 mm or less, and more preferably 30 mm or more and 70 mm or less. Further, the inner diameter of the capillary 5 is 0.1 mm or more and 1.5 mm or less, preferably 0.3 mm or more and 1.0 mm or less, and more preferably 0.5 mm or more and 0.7 mm or less.

The fluid collection volume of the capillary 5 is, for example, 0.25 μl. In this case, the length dimension is 32 mm, and the inner diameter is 0.099 mm. As another example, the fluid collection volume is 10 μl. In this case, the length dimension is 41 mm, and the inner diameter is 0.56 mm. As still another example, the fluid collection volume is 20 μl. In this case, the length dimension is 64 mm, and the inner diameter is 0.63 mm.

The capillary 5 is connected to the base end part 33 while being fitted with the base end part 33. The phrase "fitted with" as used herein includes a case where the base end part 33 is fitted into the capillary 5, and a case where the capillary 5 is fitted into the base end part 33. In the present embodiment, the base end part 33 is fitted into the capillary 5.

The inner diameter of the capillary 5 is the same as the outer diameter of the base end part 33. Therefore, the capillary 5 is supported against the base end part 33 while the base end part 33 is fitted thereinto. The overlapping dimension L2 of the capillary 5 and the base end part 33 in the state where the capillary 5 is fitted with the base end part 33 is preferably 4 mm or more. When the overlapping dimension L2 of the capillary 5 and the base end part 33 is 4 mm or more, the capillary 5 can be effectively supported against the base end part 33. However, when the capillary 5 is held, for example, by the cylindrical part 42 as in modified examples described later, the overlapping dimension of the capillary 5 and the base end part 33 may be less than 1 mm. Alternatively, there may be no overlapping part as long as the inside of the capillary 5 and the inside of base end part 33 communicate with each other.

The term "the same" used in the present specification does not mean "the same" in the strict sense of the term. The phrase "substantially the same" is also in the category of "the same" as long as the effect that the capillary 5 is fitted with the base end part 33 so that the capillary 5 is supported can be obtained. For example, when the capillary 5 is made of an elastically deformable material, the inner diameter of the capillary 5 is smaller than the outer diameter of the base end part 33 before fitting, whereas when the inner diameter of the capillary 5 and the outer diameter of the base end part 33 are almost the same after fitting, the inner diameter of the capillary 5 is supposed to be "the same" as the outer diameter of the base end part 33. Further, a case where the bodily fluid passes through the flow path 31 in the needle tube 3 by the effect of capillary action of the needle tube 3, and is then, without remaining inside the cylindrical part 42 of the needle hub 4, continuously collected into the capillary 5 from the needle tube 3 by the effect of capillary action of the capillary 5, is also included in "the same."

The material of the capillary 5 is not particularly limited, and examples include metal, synthetic resin, carbon, glass, wood, paper, cloth, rubber, and the like. However, in consideration of the workability of fluid collection, it is preferable that the material has a certain degree of hardness, water repellency, and the like.

The capillary 5 is removably attached to the base end part 33 of the needle tube 3. Therefore, the bodily fluid moving from the needle tube 3 into the capillary 5 further advances by the effect of capillary action, and reaches the end part of the capillary 5 in its longitudinal direction on a side opposite to the needle tube 3. Then, a fixed amount of bodily fluid enters inside the capillary 5; thus, a fixed amount of bodily fluid can be collected by removing the capillary 5 from the needle tube 3.

(1.2.3) Protective Member

The protective member 6 covers the circumference of the capillary 5 to protect the capillary 5. The term "protect" as used herein means protection from external forces from other members, as well as protection from powders and liquids such as chemicals and solutions, and fine stains such as lint and dust.

The protective member 6 may be flexible or rigid. The protective member 6 according to the present embodiment is composed of a hard syringe 60, which is able to properly protect the capillary 5, and allows the user to hold the syringe 60 to collect the fluid. The phrase "cover the circumference" as used in the present specification means surrounding most of the capillary 5 in its longitudinal direction, and part of the capillary 5 may protrude from the protective member 6. As long as the protective member 6 can protect the capillary 5, for example, even a case where the capillary 5 protrudes from the end part of the protective member 6 about 20% of the whole is in the category of "covering the circumference." The syringe 60 is explained below as an example of the protective member 6.

The syringe 60 is equipped with the needle part 2 to which the capillary 5 is attached, and thereby protects the capillary 5 from damage and the like. The syringe 60 has a certain degree of rigidity and is composed of, for example, synthetic resin, metal, glass, acrylic, or the like. The phrase "a certain degree of rigidity" as used herein means rigidity to the extent that the syringe can stand on its own, and if it is rigid enough to be elastically deformed, it is in the category of "having a certain degree of rigidity." Because the syringe 60 has a certain degree of rigidity, the user can carry (hold) the syringe 60 to collect the fluid. The syringe 60 has a tip part 61 to which the needle hub 4 is attached, and an outer cylindrical part 62 leading to the tip part 61.

The outer cylindrical part 62 is a portion covering the circumference of the capillary 5 in the syringe 60. The outer cylindrical part 62 is formed in a cylindrical shape with an opening surface on one end surface in its longitudinal direction, and with a tip surface 63 on the other end surface. The inner surface of the outer cylindrical part 62 has a gap from the capillary 5, and is separated from the capillary 5. The outer cylindrical part 62 covers the circumference of the capillary 5; however, the end of the capillary 5 is preferably located in the middle of the outer cylindrical part 62 in the axial direction, as in the present embodiment. The tip surface 63 of the outer cylindrical part 62 intersects with (here, almost orthogonal to) the longitudinal direction of the outer cylindrical part 62.

The tip part 61 is a portion to which the needle hub 4 is attached, as described above, and protrudes from the tip surface 63 of the outer cylindrical part 62 along the longitudinal direction of the outer cylindrical part 62. The tip part 61 is formed in a cylindrical shape. The shape of the tip part 61 is, for example, a luer-slip type, a luer-lock type, a luer-metal type, a catheter tip type, or the like. The tip part 61 in the present embodiment is formed on the central axis of the outer cylindrical part 62, but may be formed, for example, in a position deviated from the central axis of the outer cylindrical part 62.

When the needle part 2 is attached to the outer cylindrical part 62 while the capillary 5 is connected to the base end part 33 of the needle tube 3, the capillary 5 is covered by the outer cylindrical part 62. Therefore, in the bodily fluid-collecting device 1 according to the present embodiment, the capillary 5 can be prevented from dropping off when hitting other components during collection of the bodily fluid. Moreover, since the user can hold the outer cylindrical part 62 to collect the fluid, the ease of holding the bodily fluid-collecting device 1 can be improved, compared with the case without the outer cylindrical part 62.

(1.3) Method

Next, a method for collecting a bodily fluid using the bodily fluid-collecting device 1 according to the present embodiment is described. In the bodily fluid-collecting device 1 according to the present embodiment, various bodily fluids can be collected from various living bodies. As an example, a method for collecting an aqueous humor 73 of an animal is described below.

The method for collecting the aqueous humor 73 of the present embodiment comprises a first step, a second step, a third step, a fourth step, and a fifth step.

The first step is a step of performing preparation before collecting a bodily fluid. In the first step, a living body (e.g., rabbit) is retained using a retainer, and local anesthesia is applied to an eyeball 7 of the living body. The term "retain" as used herein means keeping the living body still. As the local anesthesia, for example, a 0.4% oxybuprocaine hydrochloride ophthalmic solution (produced by Santen Pharmaceutical Co., Ltd., Benoxil (registered trademark) ophthalmic solution 0.4%), or a diluted solution thereof (dilution medium: physiological saline or artificial tears, PBS: phosphate-buffered saline etc.) is ophthalmically administered to the eyeball 7 of the living body. In the method for collecting the aqueous humor 73 according to the present embodiment, the aqueous humor 73 can be repeatedly collected from one living body after a while. When repeatedly collecting the aqueous humor 73 after a while, it is preferable to use a diluted solution to minimize damage to the cornea 71 due to frequent administration of the local anesthesia. The surface of the cornea 71 tends to be rough when an undiluted ophthalmic solution is used repeatedly as the local anesthesia; however, this can be reduced by using a diluted solution.

After administration of local anesthesia, the cornea 71 is stimulated with a rounded instrument, e.g., the tip of tweezers, and the effect of local anesthesia is confirmed by confirming the disappearance of the corneal reflex. Then, a lid retractor is attached to the living body. The lid retractor prevents blinking and allows the eyelid of the living body to remain open.

Figure 3:
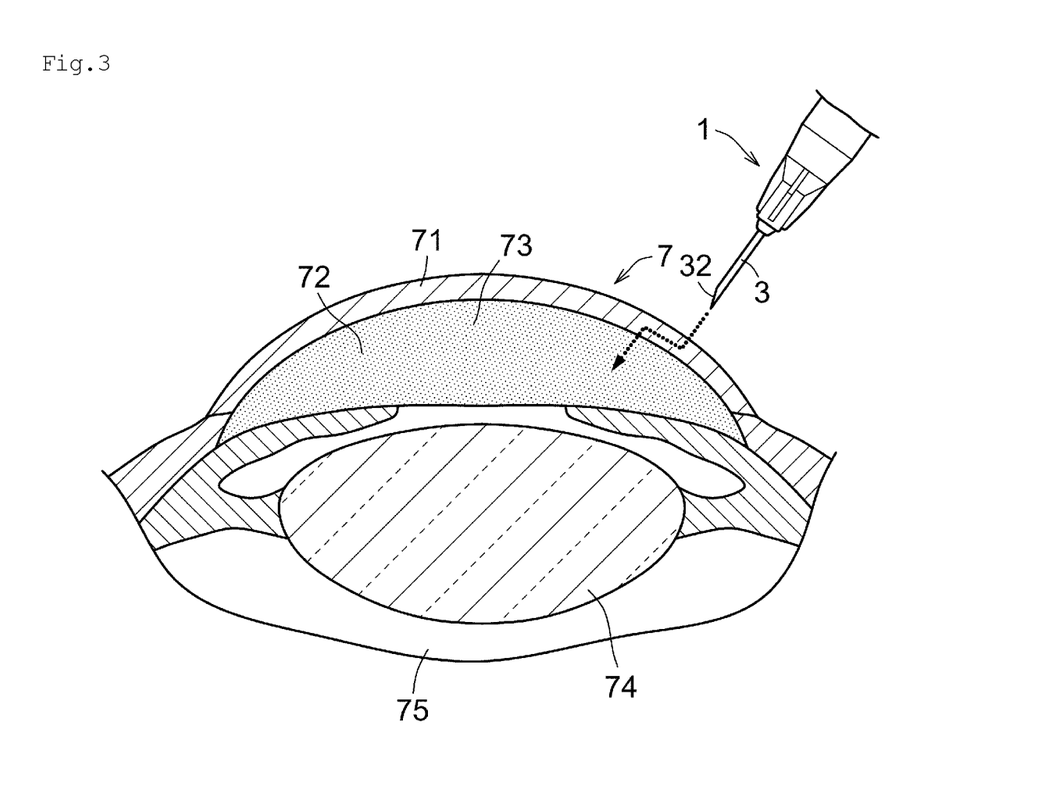
FIG. 3 is an explanatory drawing for explaining the second step of a method for collecting an aqueous humor using the bodily fluid-collecting device.

The second step is a step of inserting the needle tip 32 of the needle tube 3 into a tissue of the living body where the bodily fluid is present (here, anterior chamber 72). The needle tip 32 of the needle tube 3 is inserted by two-step puncture into the eyeball 7 with the eyelid open by the lid retractor, as shown in FIG. 3. Two-step puncture means that the needle tip 32 of the needle tube 3 is inserted into the cornea 71 in the direction along the normal line, and pushed within the thickness of the cornea 71 in the direction along the cornea 71 for a while, after which the angle is changed to the anterior chamber 72 side, and the needle tip 32 is inserted again. By two-step puncture, leakage of the aqueous humor 73 from the cornea 71 can be suppressed even after the needle tube 3 is withdrawn. In FIG. 3, numeral 74 denotes the lens, and numeral 75 denotes the vitreous body.

Figure 4:
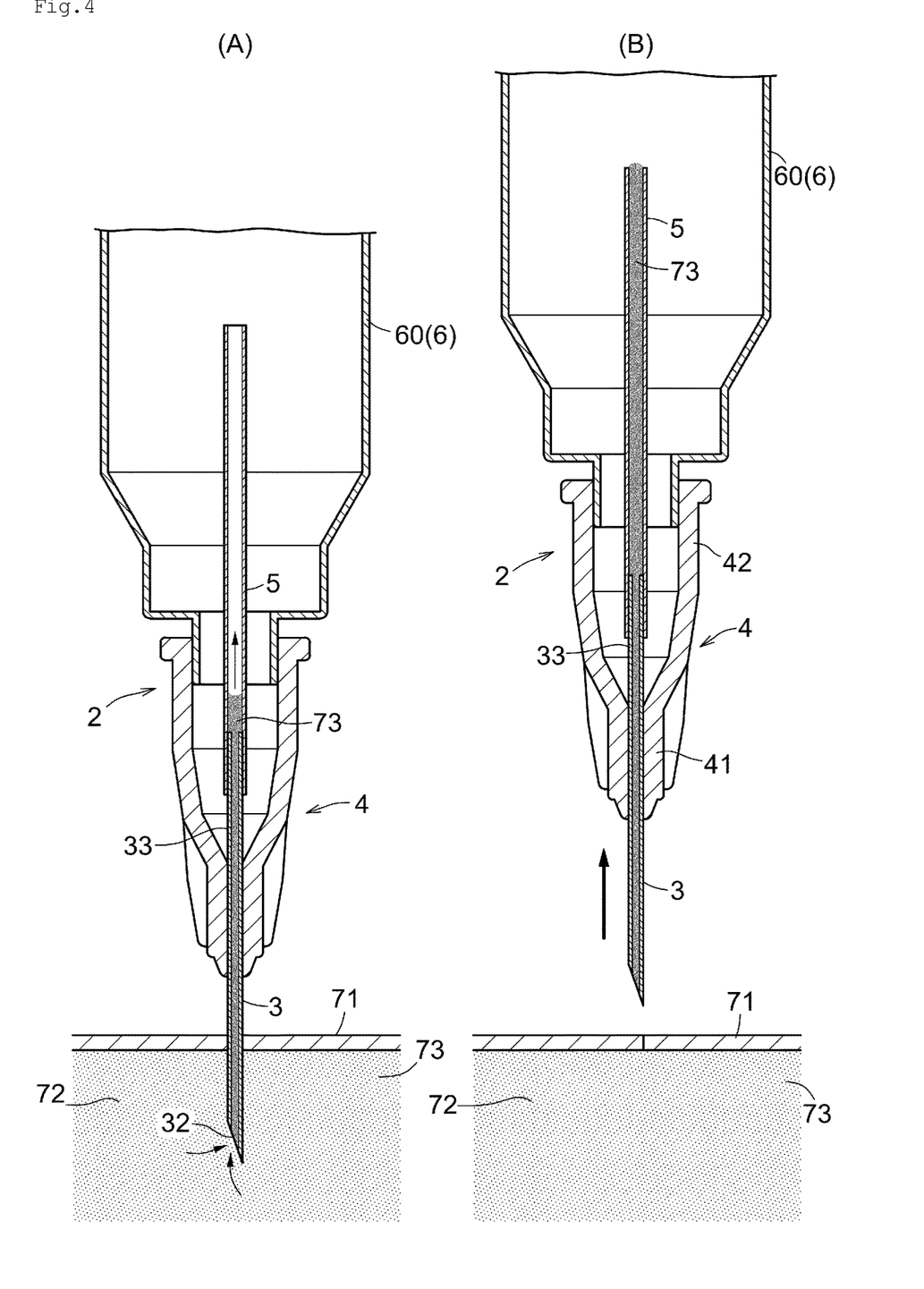

The third step is a step of withdrawing the needle tip 32 from the inside of the tissue (inside of the anterior chamber 72) after the capillary 5 is filled with the bodily fluid (here, the aqueous humor 73). When the needle tip 32 is inserted into the anterior chamber 72 in the second step, the aqueous humor 73 proceeds inside the needle tube 3 by the effect of capillary action, and the liquid level approaches the base end part 33, as shown in FIG. 4 (A). Then, the aqueous humor 73 reaches the inside of the capillary 5, and the aqueous humor 73 fills the capillary 5 by the effect of capillary action. The user confirms that the aqueous humor 73 reaches an end part of the capillary 5 in its longitudinal direction on a side opposite to the needle tube 3 side, as shown in FIG. 4 (B), and then withdraws the needle tube 3 from the inside of the anterior chamber 72.

In the second and third steps, the direction of insertion of the needle tube 3 into the anterior chamber 72 is not particularly limited; however, it is preferable to keep it as vertical as possible. This is because it is preferable to avoid, as far as possible, the capillary 5 from dropping off from the needle tube 3 when the needle tube 3 is inserted into the anterior chamber 72, or in the process of drawing the aqueous humor 73 into the needle tube 3 and the capillary 5.

The fourth step is a step of removing the capillary 5 from the needle tube 3. After the third step, the inside of the capillary 5 is filled with a fixed amount of aqueous humor 73; thus, a fixed amount of aqueous humor 73 can be easily collected from the capillary 5 by removing the capillary 5 from the needle tube 3. At this time, in order to further improve workability, it is preferable to remove the needle part 2 from the syringe 60 before removing the capillary 5 from the needle tube 3.

The fifth step is a step of extracting the aqueous humor 73 filled in the capillary 5. A fixed amount of aqueous humor 73 filled in the capillary 5 can be extracted from the capillary 5, for example, by blowing air into the capillary 5 from one end part in its longitudinal direction to pressurize the inside of the capillary 5. The aqueous humor 73 is received, for example, by a container such as a microtube. At this time, the capillary 5 contains a fixed amount of aqueous humor 73 necessary for examination. Accordingly, if an organic solvent etc. for pretreatment for analysis is previously prepared in the microtube, the aqueous humor 73 can be directly supplied from the capillary 5 into the organic solvent etc. for pretreatment.

Thereafter, the lid retractor is removed from the living body, and it is confirmed whether the aqueous humor 73 does not leak from the eyeball 7, and whether the living body does not feel excessive pain. Then, the first to fifth steps are repeated after a while. This makes it possible to collect the aqueous humor sequentially.

In the method for collecting the aqueous humor 73 according to the present embodiment, the outer diameter of the needle tube 3 is small, and the amount of aqueous humor 73 collected at one time is also small. Therefore, it can suppress the shape change of the cornea and the occurrence of fibrin mass and inflammation in the anterior chamber, resulting in a good prognosis in the living body. As a result, it is possible to collect bodily fluids, which have been difficult to collect. Further, the ability to repeatedly collect bodily fluids can significantly reduce the number of living bodies required for examination, test, etc.

(2) MODIFIED EXAMPLES

The above embodiment is merely one of the various embodiments of the present invention. The embodiment can be changed in various ways depending on design etc., as long as the object of the present invention can be achieved. Modified examples of the embodiment are described below. The modified examples described below can be applied in combination as appropriate.

(2.1) Modified Example 1

Figure 5:
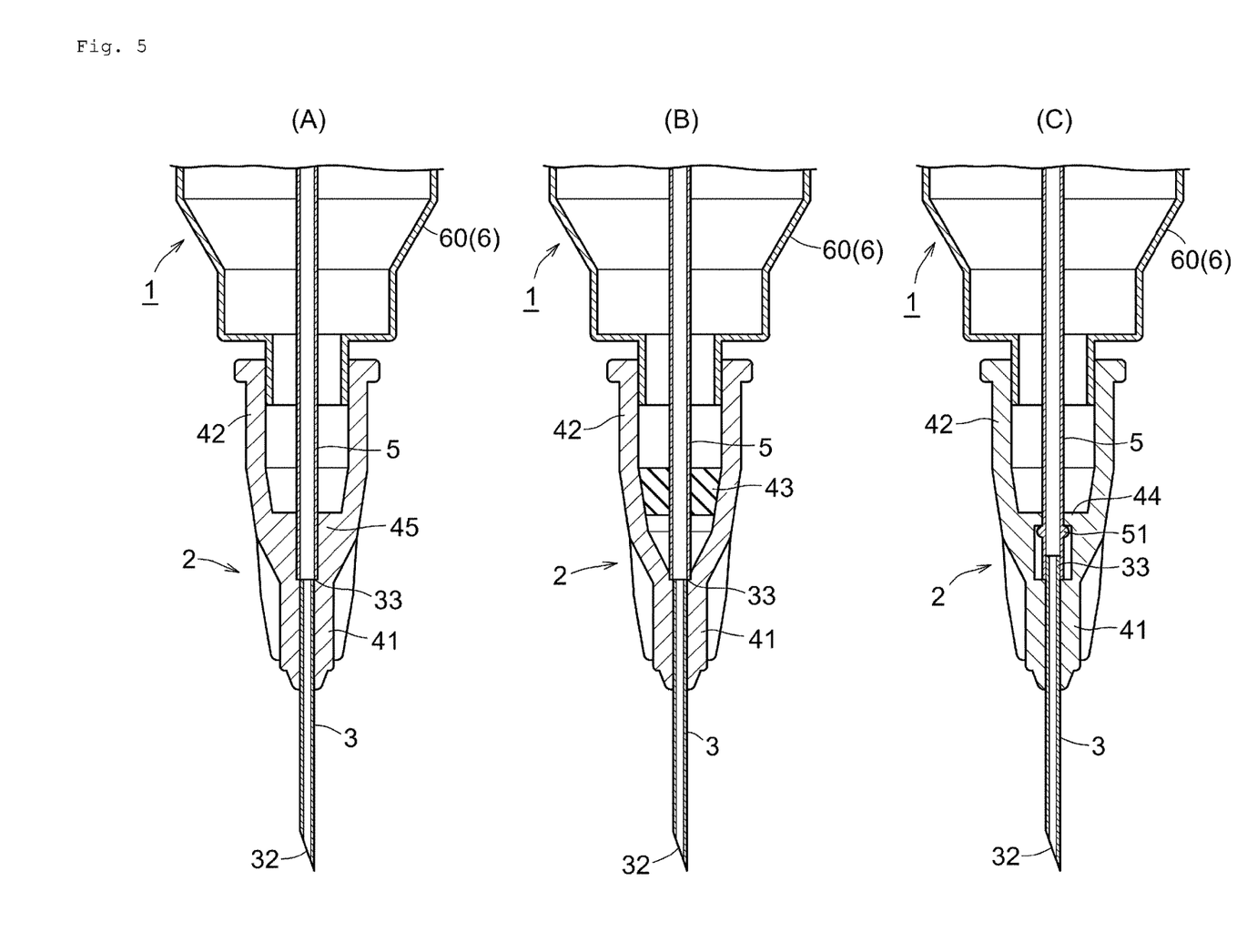

In the bodily fluid-collecting device 1 according to the above embodiment, the base end part 33 of the needle tube 3 protrudes from the holding part 41, and the capillary 5 is fitted with the protruding base end part 33. In this modified example, the capillary 5 is removably fitted into the cylindrical part 42 of the needle hub 4, as shown in FIG. 5 (A). In this state, the base end part 33 and the capillary 5 are connected with each other.

The cylindrical part 42 has a fitting part 45 into which the capillary 5 is fitted. The fitting part 45 may be composed of a block body with a hole into which the capillary 5 can be fitted, in the cylindrical part 42, or a plurality of ribs formed radially around the central axis of the cylindrical part 42. When the capillary 5 is fitted into the fitting part 45, the capillary 5 is connected with the base end part 33 of the needle tube 3. In this modified example, the "base end part 33" refers to an end surface of the needle tube 3 in its longitudinal direction on a side opposite to the needle tip 32 side. Unlike the above embodiment, the capillary 5 is not fitted with the base end part 33; however, they are communicated with each other, namely removably connected with each other.

With the bodily fluid-collecting device 1 according to this modified example, a small and fixed amount of bodily fluid can be collected using the capillary 5, in the same manner as the above embodiment.

(2.2) Modified Example 2

In the bodily fluid-collecting device 1 according to Modified Example 1, the capillary 5 is fitted with the fitting part 45 integrally formed with the cylindrical part 42. This modified example is different from Modified Example 1 in that the capillary 5 is held by a holding member 43 attached to the cylindrical part 42.

The holding member 43 is interposed between the inner peripheral surface of the cylindrical part 42 and the capillary 5, and removably attaches the capillary 5 to the cylindrical part 42. The holding member 43 is formed in a cylindrical shape, and holds the capillary 5 in its central through hole. The holding member 43 is fitted into the cylindrical part 42 to be thereby fixed to the cylindrical part 42. The holding member 43 is made of, for example, elastomer, synthetic resin, metal, wood, paper, or the like. The capillary 5 is removably connected to the base end part 33 while being held by the holding member 43.

(2.3) Modified Example 3

In the bodily fluid-collecting devices 1 according to Modified Examples 1 and 2, the capillary 5 is fitted by means of the fitting part 45 integrally formed with the cylindrical part 42 or the holding member 43 attached between the capillary 5 and the cylindrical part 42. In this modified example, the capillary 5 uses a convex portion 51 formed on the capillary 5 and a hook portion 44 formed in the cylindrical part 42 to prevent the needle tube 3 from being released in the longitudinal direction.

The convex portion 51 protrudes outward in the radial direction from the outer peripheral surface of the capillary 5. The convex portion 51 in the present embodiment is composed of a ridge continuous in the circumferential direction, but may be a plurality of convex portions formed at intervals in the circumferential direction.

The hook portion 44 is hooked on the convex portion 51 to prevent the capillary 5 from moving away from the needle tube 3 in the longitudinal direction. However, when a force not less than a predetermined force is applied to the capillary 5 on the side away from the needle tube 3 in the longitudinal direction, the hook portion 44 releases the engagement with the convex portion 51, and the capillary 5 drops off from the base end part 33.

As a further modification of Modified Example 3, a groove may be formed in place of the convex portion 51 of the capillary 5, a protrusion to be fitted into the groove may be formed in the cylindrical part 42, and the groove and the protrusion may be used to prevent the capillary 5 from being released.

(2.4) Other Modified Examples

Other modified examples are listed below.

In the above embodiment, the needle part 2 is separated from the syringe 60; however, in the present invention, the needle part 2 and the protective member 6 may be integrated with each other. Further, the bodily fluid-collecting device 1 according to the above embodiment comprises the protective member 6; however, the protective member 6 may be omitted in the present invention.

Moreover, the shape of the protective member 6 is not limited to a cylindrical shape, and may be a square cylindrical shape, a box shape, a bag shape, a spherical shape, or the like. The shape is not particularly limited.

The needle part 2 according to the above embodiment comprises the needle hub 4 that supports the needle tube 3. However, in the present invention, the needle hub 4 may be omitted; that is, the needle part 2 may consist of the needle tube 3.

The capillary 5 according to the above embodiment is fitted with the base end part 33; however, for example, the capillary 5 and the base end part 33 may be reinforcingly attached using an adhesive to increase the fixing strength.

In the present specification, expressions with "almost," such as "almost parallel" or "almost orthogonal," are sometimes used. For example, "almost parallel" means substantially "parallel," and includes not only a strictly parallel state but also a parallel state with an error of several degrees. The same applies to other expressions with "almost."

Further, in the present specification, expressions that are distinguished by the presence of "part," such as "end part" and "end," are used. For example, "end part" refers to a portion with a certain range including the "end." The same applies to other expressions with "part."

(3) SUMMARY

As described above, the bodily fluid-collecting device 1 according to the first embodiment comprises a needle part 2 having a needle tube 3 with a needle tip 32, and a capillary 5 removably connected to a base end part 33 of the needle tube 3 in its longitudinal direction on a side opposite to the needle tip 32.

According to this embodiment, when the needle tip 32 is inserted into a living body, the bodily fluid is drawn into the capillary 5 by the effect of capillary action. Since the amount of bodily fluid that fills the capillary 5 is constant depending on the volume of the capillary 5, a fixed amount of bodily fluid can be collected by removing the capillary 5 from the needle tube 3. Further, due to the collection of a small amount of bodily fluid and the use of the needle tube 3 that is thinner than conventional ones, damage to the living body can be minimized. As a result, according to this embodiment, a fixed amount of bodily fluid can be collected while minimizing damage to the living body. Therefore, the bodily fluid can be repeatedly and sequentially collected from one living body. Further, due to taking advantage of the effect of capillary action, it is not necessary to pull the plunger like before, which can improve workability. In addition, it is possible to eliminate damage to the living body caused by the negative pressure generated by pulling the plunger. This also contributes to the minimization of damage to the living body.

In the bodily fluid-collecting device 1 according to the second embodiment, in the first embodiment, the needle part 2 has a holding part 41 that is in contact with the outer peripheral surface of the needle tube 3 to hold the needle tube 3. The base end part 33 of the needle tube 3 protrudes from the holding part 41 in the longitudinal direction of the needle tube 3. The capillary 5 is connected to the base end part 33 while being fitted with the base end part 33.

According to this embodiment, the capillary 5 can be easily connected to the base end part 33 and can be easily removed, which ensures good workability.

In the bodily fluid-collecting device 1 according to the third embodiment, in the second embodiment, the protrusion dimension of the base end part 33 from the holding part 41 is 1 mm or more and 13 mm or less.

According to this embodiment, the capillary 5 can be supported while the capillary 5 is connected to the base end part 33.

In the bodily fluid-collecting device 1 according to the fourth embodiment, in the second or third embodiment, the inner diameter of the capillary 5 is the same as the outer diameter of the base end part 33.

According to this embodiment, the capillary 5 can be effectively supported by the base end part 33.

In the bodily fluid-collecting device 1 according to the fifth embodiment, in any one of the first to fourth embodiments, the outer diameter of the needle tube 3 is 0.18 mm or more and 0.30 mm or less.

According to this embodiment, the fluid collection volume of the capillary 5 is small; thus, even if the outer diameter of the needle tube 3 is reduced, a sufficient amount of bodily fluid can be quickly collected. As a result, damage to the living body can be suppressed.

In the bodily fluid-collecting device 1 according to the sixth embodiment, in the first embodiment, the needle part 2 has a needle hub 4 that supports the needle tube 3. The needle hub 4 has a holding part 41 that is in contact with the outer peripheral surface of the needle tube 3 to hold the needle tube 3, and a cylindrical part 42 leading to the holding part 41. The capillary 5 is connected to the base end part 33 while being fitted into the cylindrical part 42.

According to this embodiment, the capillary 5 can be supported by the cylindrical part 42. Thus, the base end part 33 of the needle tube 3 may be shortened or lengthened; in short, the design freedom of the length of the base end part 33 of the needle tube 3 can be increased.

In the bodily fluid-collecting device 1 according to the seventh embodiment, in the first embodiment, the needle part 2 has a needle hub 4 that supports the needle tube 3. The needle hub 4 has a holding part 41 that is in contact with the outer peripheral surface of the needle tube 3 to hold the needle tube 3, a cylindrical part 42 leading to the holding part 41, and a holding member 43 disposed inside the cylindrical part 42 and removably holding the capillary 5. The capillary 5 is connected to the base end part 33 while being held by the holding member 43.

According to this embodiment, the capillary 5 can be effectively fixed to the cylindrical part 42 by the holding member 43. Further, since the holding member 43 and the cylindrical part 42 are separate members, the holding member 43 can be easily produced, and can support various foams of the needle parts 2.

In the bodily fluid-collecting device 1 according to the eighth embodiment, in any one of the first to seventh embodiments, the needle part 2 has a needle hub 4 that supports the needle tube 3. The bodily fluid-collecting device 1 further comprises a protective member 6 attached to the needle hub 4 and covering the circumference of the capillary 5.

According to this embodiment, the capillary 5 can be properly protected.

In the bodily fluid-collecting device 1 according to the ninth embodiment, in the eighth embodiment, the protective member 6 is a syringe 60 having a tip part 61 attached to the needle hub 4, and an outer cylindrical part 62 covering the circumference of the capillary 5.

According to this embodiment, the capillary 5 can be prevented from dropping off when hitting other components during collection of the bodily fluid. Moreover, the ease of holding the bodily fluid-collecting device 1 can be improved, compared with the case without the outer cylindrical part 62.

The method for collecting a bodily fluid according to the tenth embodiment is a method for collecting a bodily fluid using the bodily fluid-collecting device 1 according to any one of the first to ninth embodiments. The method for collecting a bodily fluid comprises the steps of inserting the needle tip 32 of the needle tube 3 into a tissue of a living body where the bodily fluid is present, withdrawing the needle tip 32 from the tissue after the capillary 5 is filled with the bodily fluid, removing the capillary 5 from the needle tube 3, and extracting the bodily fluid filled in the capillary 5.

According to this embodiment, a small and fixed amount of bodily fluid can be collected from a living body, and damage to the living body can be suppressed. As a result, the bodily fluid can be repeatedly and sequentially collected from one living body, and it is possible to obtain data over time for each individual. Accordingly, it is possible to avoid errors in data interpretation due to individual variations. As a result, the number of required living bodies can be reduced.

The method for collecting an aqueous humor 73 according to the eleventh embodiment is a method for collecting the aqueous humor 73 using the bodily fluid-collecting device 1 according to any one of the first to ninth embodiments. The method for collecting the aqueous humor 73 comprises the steps of inserting the needle tip 32 of the needle tube 3 into an anterior chamber 72 of a living body, withdrawing the needle tip 32 from the anterior chamber 72 after the capillary 5 is filled with the aqueous humor 73, removing the capillary 5 from the needle tube 3, and extracting the aqueous humor 73 filled in the capillary 5.

According to this embodiment, a small and fixed amount of aqueous humor 73 can be collected, and damage to the living body can be suppressed. As a result, the aqueous humor 73 can be repeatedly and sequentially collected from one living body, and it is possible to obtain data sequentially for each individual. Accordingly, it is possible to avoid errors in data interpretation due to individual variations. As a result, the number of required living bodies can be reduced.

The configurations of the second to ninth embodiments are not essential for the bodily fluid-collecting device 1, and can be omitted as appropriate.

(4) Example

The present invention is described in more detail below with reference to an Example. However, the bodily fluid-collecting device, method for collecting a bodily fluid, and method for collecting an aqueous humor according to the present invention are not limited to the following Example.

(4.1) Ophthalmic Administration

Using a micropipette, a 0.5% timolol maleate sustained ophthalmic solution (produced by Santen Pharmaceutical Co., Ltd., Timoptol (registered trademark) XE ophthalmic solution 0.5%) was administered as a single dose of 40 µl near the upper portion of the bulbar conjunctiva of rabbit eyeballs retained using a retention can. The administration was performed on both eyes.

(4.2) Aqueous Humor Collection

A rabbit was retained using a retention can. 30 µl of a 10-fold diluted solution (dilution medium: physiological saline) of a 0.4% oxybuprocaine hydrochloride ophthalmic solution (produced by Santen Pharmaceutical Co., Ltd., Benoxil (registered trademark) ophthalmic solution 0.4%) was ophthalmically administered to the retained rabbit, and local anesthesia was applied. After gently stimulating the cornea with the tip of tweezers and confirming the disappearance of the corneal reflex, a lid retractor was attached.

In the Example, a device with a 20-µl capillary attached to a 34 G injection needle was used as the bodily fluid-collecting device. After retaining the eyeball by sandwiching the upper bulbar conjunctiva with tweezers, the needle tip of the bodily fluid-collecting device was inserted into the anterior chamber via the cornea by two-step puncture while checking the curved surface of the cornea.

After confirming that the capillary was filled with the aqueous humor, the needle tip was withdrawn from the anterior chamber. Thereafter, the syringe was removed from the needle hub, and the capillary was removed from the needle tube. Then, the aqueous humor filled in the capillary was transferred into a microtube by means of pneumatic pressure. The aqueous humor transferred into the microtube was cryopreserved until drug concentration measurement was performed.

The lid retractor was removed from the rabbit, and it was confirmed whether the aqueous humor did not leak from the eyeballs of the rabbit, and whether the living body did not feel excessive pain. From one of both eyes, the aqueous humor was collected sequentially at 0.25 hours, 0.5 hours, 1 hour, 2 hours, and 4 hours after ophthalmic administration (this is referred to as "Method 1"). From the other eye, the aqueous humor was collected only at a point in time 4 hours after ophthalmic administration (this is referred to as "Method 2").

(4.3) Drug Concentration Measurement

10 µl of the collected aqueous humor was used for analysis. After deproteinizing each sample, the timolol concentration of the aqueous humor was measured using the LC/MS/MS method.

(4.4) Results

Figure 6:
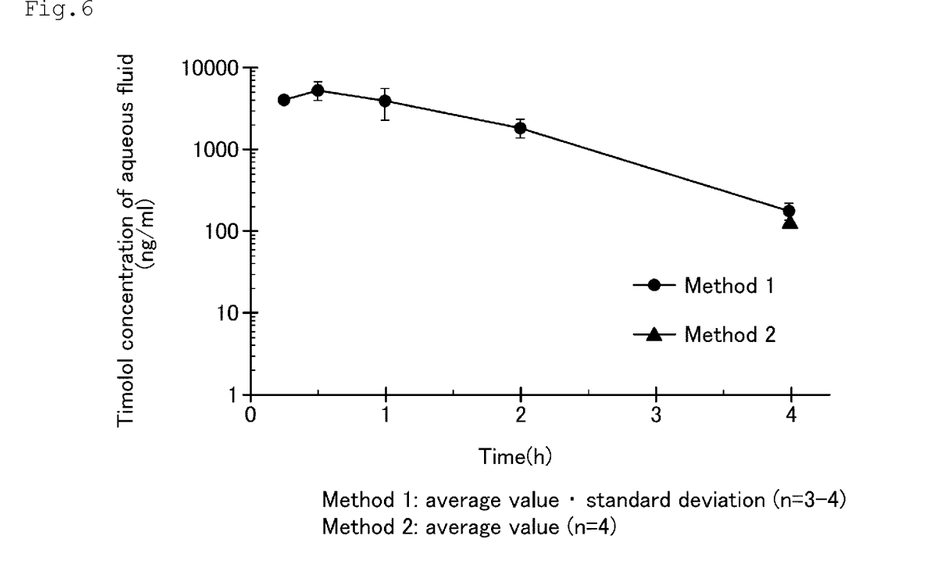
FIG. 6 is a graph showing the measurement results of an Example.

FIG. 6 shows the results of Methods 1 and 2. As can be seen from FIG. 6, the timolol concentration of the aqueous humor at the time of the final collection when the aqueous humor was repeatedly collected from the same eye using the bodily fluid-collecting device was equivalent to the timolol concentration of the aqueous humor when the aqueous humor was collected only at one point in time as Method 2.

This revealed that the aqueous humor can be repeatedly collected from one living body by using the bodily fluid-collecting device according to the Example. It was also found that the method for collecting an aqueous humor using the bodily fluid-collecting device according to the Example was also useful for pharmacokinetic evaluation.

REFERENCE SIGNS LIST

1: Bodily fluid-collecting device
2: Needle part
3: Needle tube
32: Needle tip
33: Base end part
4: Needle hub
41: Holding part
42: Cylindrical part
43: Holding member
5: Capillary
6: Protective member
61: Tip part
62: Outer cylindrical part
72: Anterior chamber
73: Aqueous humor

The invention claimed is:

1. A bodily fluid collection device for collecting a fixed amount of a bodily fluid comprising an aqueous humor, the bodily fluid collection device comprising:
a needle part having a needle tube with a needle tip;
a linear capillary capable of containing the aqueous humor therein; and
a protector,
wherein:
a first end of the linear capillary in a longitudinal direction of the linear capillary is open;
a second end of the linear capillary in the longitudinal direction of the linear capillary is open;
the first end of the linear capillary in the longitudinal direction of the linear capillary is removably connected to a base end part of the needle tube in a longitudinal direction of the needle tube on a side opposite to the needle tip;
the needle part has a holding part that is in contact with an outer peripheral surface of the needle tube and configured to hold the needle tube;
the base end part of the needle tube protrudes from the holding part of the needle part in the longitudinal direction of the needle tube;
the linear capillary is configured such that an inner peripheral surface of the linear capillary is in contact with the outer peripheral surface of needle tube at the base end part of the needle tube, and an inner diameter of the linear capillary is constant over an entire length of the linear capillary in the longitudinal direction of the linear capillary;

wherein the inner diameter of the linear capillary is 0.5 mm or more and 0.7 mm or less;
the linear capillary has a length of 30 mm or more and 70 mm or less;
the needle part has a needle hub that supports the needle tube;
the protector is removably attached to the needle hub and covers a circumference of the linear capillary;
the protector has: (i) a tip part removably attached to the needle hub; and (ii) an outer cylindrical part having a first longitudinal end connected to the tip part and a second longitudinal end;
an inner surface of the outer cylindrical part has a same diameter from at least a center in the longitudinal direction of the linear capillary to the second longitudinal end;
the linear capillary is composed of only one linear capillary;
the linear capillary is supported only by the base end part of the needle tube;
an entirety of an inner surface of the tip part of the protector is spaced apart from the linear capillary; and
an entirety of the inner surface of the outer cylindrical part is spaced apart from the linear capillary.

2. The bodily fluid collection device according to claim 1, wherein a protrusion amount of the base end part of the needle tube from the holding part of the needle part is 1 mm or more and 13 mm or less.

3. The bodily fluid collection device according to claim 1, wherein the linear capillary is configured to cause a capillary action.

4. The bodily fluid collection device according to claim 1, wherein:
the needle hub has: (i) the holding part of the needle part; and (ii) a cylindrical part that leads to the holding part of the needle part;
the cylindrical part of the needle hub has an open end; and
the tip part of the protector is cylindrical and removably fitted into the open end of the cylindrical part of the needle hub.

5. The bodily fluid collection device according to claim 1, wherein the second end of the linear capillary is closer to a center of the protector than the second longitudinal end of the outer cylindrical part of the protector.

6. The bodily fluid collection device according to claim 1, wherein the linear capillary protrudes from the needle hub.

7. The bodily fluid collection device according to claim 1, wherein the second longitudinal end of the outer cylindrical part is open.

8. A method for collecting a bodily fluid using the bodily fluid collection device according to claim 1, the method comprising:
preparing the bodily fluid collection device, the linear capillary being connected to the base end part of the needle tube;
after preparing the bodily fluid collection device, inserting the needle tip of the needle tube into a tissue of a living body where the bodily fluid is present;
withdrawing the needle tip from the tissue of the living body after the linear capillary is filled with the bodily fluid;
removing the linear capillary from the needle tube; and
extracting the bodily fluid filled in the linear capillary.

* * * * *